United States Patent [19]

Casarcia et al.

[11] Patent Number: 4,864,239
[45] Date of Patent: Sep. 5, 1989

[54] CYLINDRICAL BEARING INSPECTION

[75] Inventors: Dominick A. Casarcia; Robert F. Feldman, both of Cincinnati, Ohio

[73] Assignee: General Electric Company, Cincinnati, Ohio

[21] Appl. No.: 557,982

[22] Filed: Dec. 5, 1983

[51] Int. Cl.[4] .............................................. G01R 33/00
[52] U.S. Cl. .................... 324/262; 324/237; 324/226; 901/16; 901/29; 901/49
[58] Field of Search ............... 324/207, 208, 225–243, 324/260–262; 414/749; 901/16, 29, 41, 49, 17, 44, 46

[56] References Cited

U.S. PATENT DOCUMENTS

| | | | |
|---|---|---|---|
| 3,401,332 | 9/1968 | McClurg et al. | 324/227 |
| 3,487,298 | 12/1969 | Gill et al. | 324/238 |
| 3,727,119 | 4/1973 | Stanley et al. | 901/44 X |
| 3,921,065 | 11/1975 | Rawlins et al. | 324/238 |
| 3,939,404 | 2/1976 | Tait | 324/226 |
| 4,042,877 | 8/1977 | Sieverin | 324/226 |
| 4,103,222 | 7/1978 | Phillips et al. | 324/207 |
| 4,125,943 | 11/1978 | Ando | 324/207 X |
| 4,206,391 | 6/1980 | Varacins | 324/262 X |
| 4,229,136 | 10/1980 | Panissidi | 901/29 X |
| 4,247,819 | 1/1981 | Shimada et al. | 324/233 |
| 4,314,203 | 2/1982 | Haberlein | 324/238 X |
| 4,325,026 | 4/1982 | Cooper Jr. et al. | 324/232 |
| 4,337,431 | 6/1982 | Hale | 324/238 X |
| 4,349,182 | 9/1982 | Blackburn | 901/41 X |
| 4,488,435 | 12/1984 | Kastl et al. | 414/749 X |

Primary Examiner—Reinhard J. Eisenzopf
Assistant Examiner—W. Edmonds
Attorney, Agent, or Firm—Derek P. Lawrence; Nathan D. Herkamp

[57] ABSTRACT

An apparatus for the inspection of a stack of cylindrical objects such as roller bearings, uses an eddy current probe. The probe is positioned at an angle with respect to the surfaces of the objects in order to achieve an acceptable signal and then the objects are rotated while the probe is advanced along them to fully scan the surfaces.

7 Claims, 4 Drawing Sheets

CYLINDRICAL BEARING INSPECTION

The present invention relates to the eddy current inspection of roller bearings.

BACKGROUND OF THE INVENTION

Cylindrical objects such as roller bearings are commonly inspected for flaws by using eddy current probes. An eddy current probe generates a time-varying electromagnetic field within the metal of the bearing. If the shape of the metal changes, as when the electromagnetic field encounters a crack, the magnetic coupling between the eddy current probe and the bearing is altered. This alteration is detectable and indicates the presence of the crack.

In the case of high-performance roller bearings, such as bearings used in gas turbine aircraft engines, it is desirable to inspect 100% of the surfaces of such bearings, rather than to inspect only sample regions of the surfaces, as is sometimes done.

OBJECTS OF THE INVENTION

It is an object of the present invention to provide a new and improved apparatus for the examination of cylindrical objects.

It is a further object of the present invention to provide a new and improved apparatus for the eddy current inspection of roller bearings.

SUMMARY OF THE INVENTION

In one form of the present invention, a stack of cylindrical objects, such as roller bearings, is rotated at a constant speed. An eddy current probe is placed against the stack and, following one revolution of the stack, is advanced a predetermined increment along the surface of the stack in the axial direction. The rotation-increment process is repeated until the entire stack is scanned.

DETAILED DESCRIPTION OF THE PRESENT INVENTION

Figure 1:
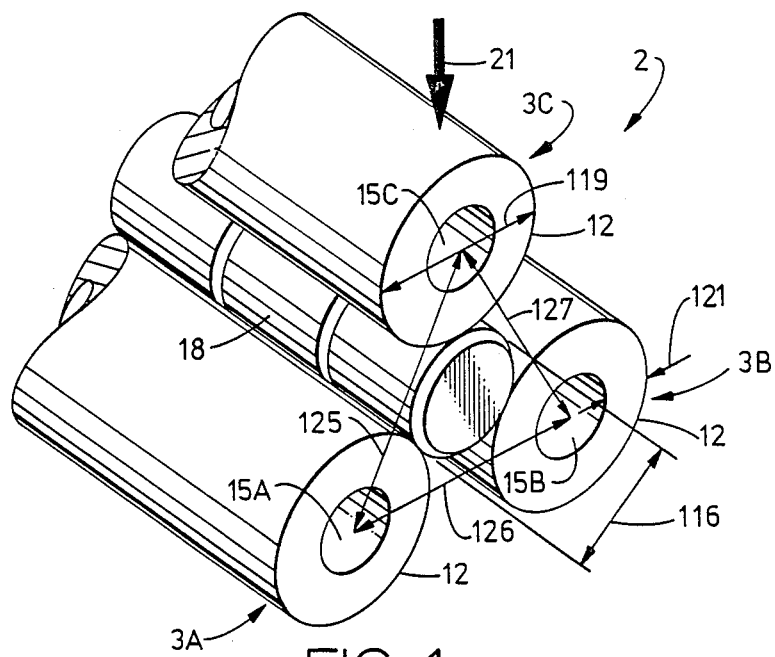
FIG. 1 illustrates a cradle supporting a stack of roller bearings.

FIG. 1 illustrates part of the present invention, namely, a cradle 2. Cylindrical rollers 3A–C each bear a sleeve 12 of resilient, high friction material. The sleeves surround cylinders 15A–C, and the latter are preferably constructed of a harder material, such as steel. The material of which sleeves 12 are composed is preferably AF50 urethane rubber, available from Parkway Products, Inc., located in Cincinnati, Ohio 45231. The rollers 3A–C surround and contact a cylindrical object 18, which can be a roller bearing. Rotation of one or more of the rollers 3A–C, by virtue of the frictional contact between them and the bearing 18, forces the bearing 18 to rotate along with the rotating rollers 3A–C. Preferably, rollers 3A and B are driven by a power source (not shown in FIG. 1) and roller 3C acts as an idler inasmuch as the latter roller applies pressure to the bearing in the direction of arrow 21 thus forces the bearing 18 into contact with rollers 3A and B, thus increasing the forces of friction between the latter rollers and bearing 18. The features just described will now be elaborated upon in greater detail with reference to FIG. 2.

Figure 2:
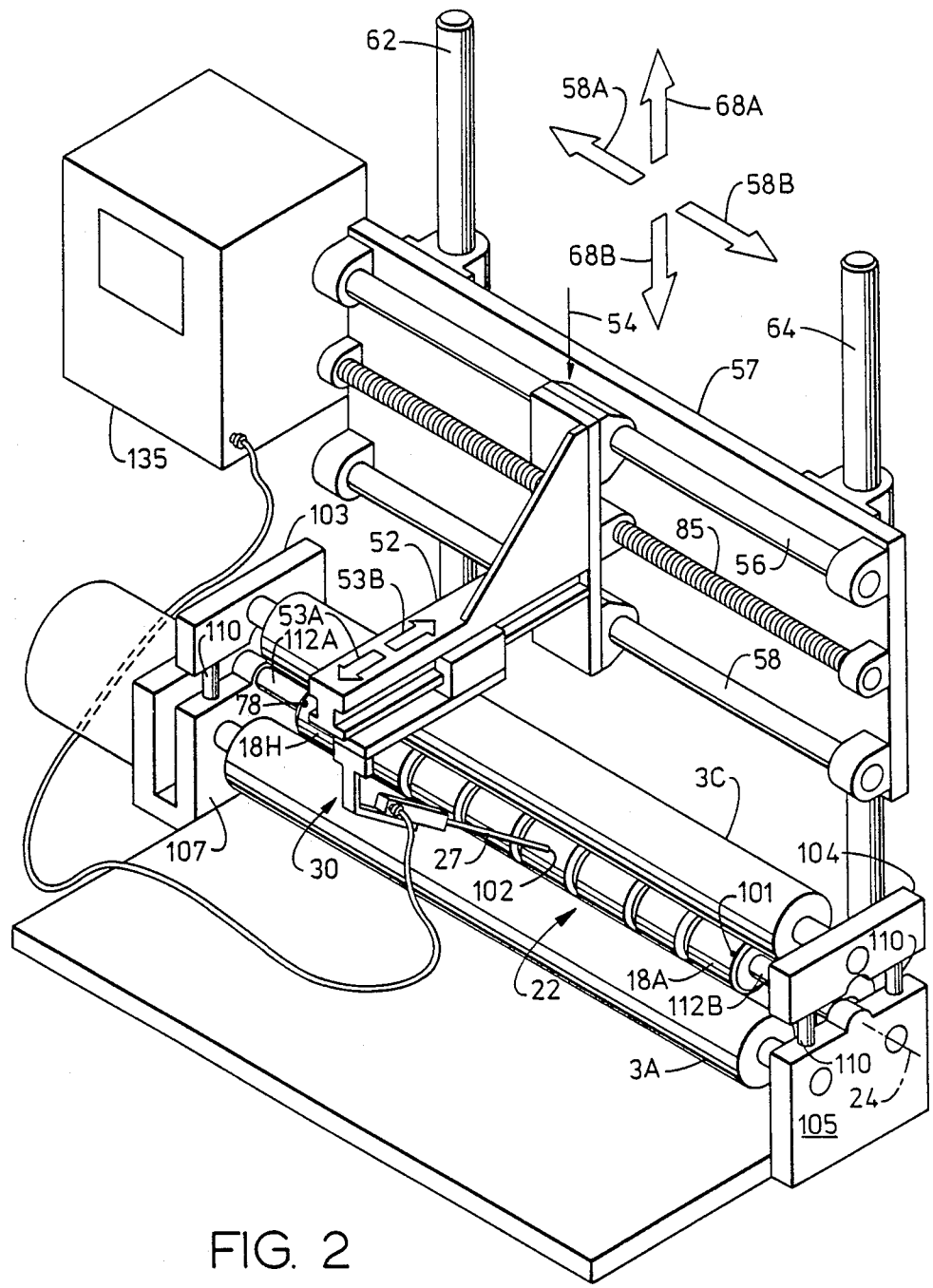
FIG. 2 illustrates one form of the present invention.

FIG. 2 illustrates an array 22 of roller bearings 18A–H which are coaxial on axis 24. As stated above, the rotation of rollers 3A and B in FIG. 1 (roller 3B is obscured from view by bearings 18A–H in FIG. 2) causes the roller bearings 18A–H to rotate.

Figure 3:
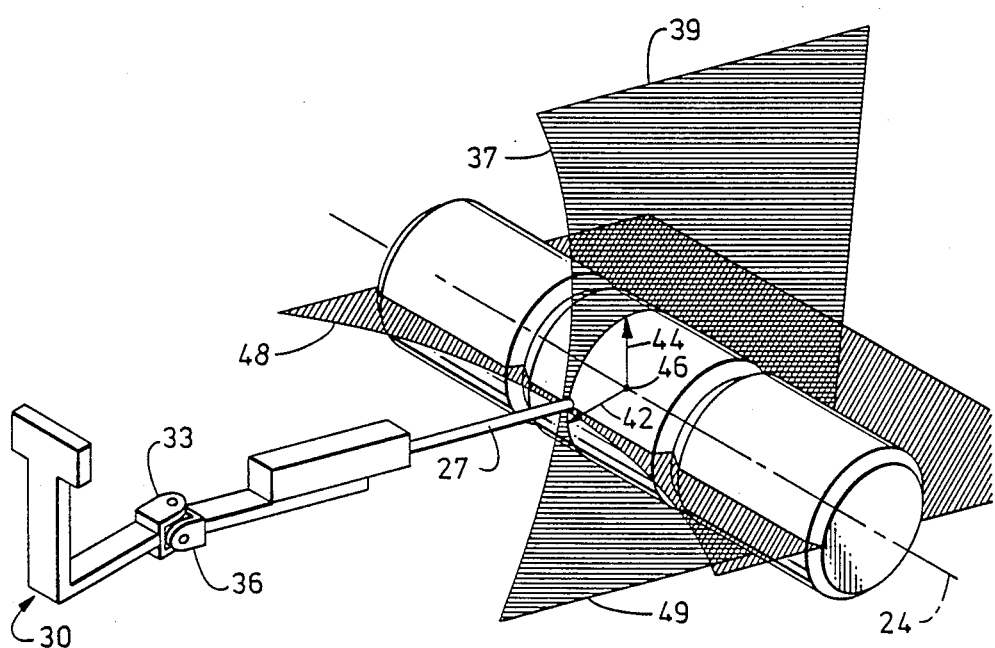
FIG. 3 illustrates two planes of rotation of the eddy current probe in the present invention.

A sensor such as eddy current probe 27 is supported by a bracket 30. The support of the eddy current probe 27 is shown in greater detail in FIG. 3, wherein the bracket 30 provides two pivot points 33 and 36 about which the eddy current probe can rotate. Pivot point 36 allows the probe 27 to rotate along a path 37 in a plane 39 which is termed a radial plane of the bearing 18, because the plane 39 contains, and is defined by, two radii 42 and 44 which emanate from the same point 46 on the axis 24 of the bearings 18. Also, probe 27 can rotate about pivot point 33, along path 48 in plane 49, which is termed an axial plane, because this plane 49 is parallel to axis 24 or contains axis 24. One purpose of the two degrees of motion of probe 27 along paths 37 and 48 will be later discussed in greater detail.

The bracket 30 in FIG. 2 is slidable along a first rail 52 so that the probe 27 may travel in the direction shown by arrows 53A and B. The first rail 52 is supported by a carriage 54 which is, in turn, supported by second and third rails 56 and 58 such that the carriage 54 can move in the directions shown by arrows 58A and B, parallel to the axis 24. Second and third rails 56 and 58 are in turn supported by a rail bed 57. This rail bed is supported by fourth and fifth rails 62 and 64 so that second and third rails 56 and 58 can move in the directions of arrows 68A and 68B, thereby moving the eddy current probe 27 in the same directions.

Fourth and fifth rails 62 and 64 have just been described; however, the term "rails" has been used for ease of explanation. In the preferred embodiment, hydraulic pistons (not shown) replace fourth and fifth rails 62 and 64 to provide the function of moving rail bed 57 in the directions of arrows 68A and B. The operation of the embodiment depicted in FIG. 1 will now be discussed.

Figure 4:
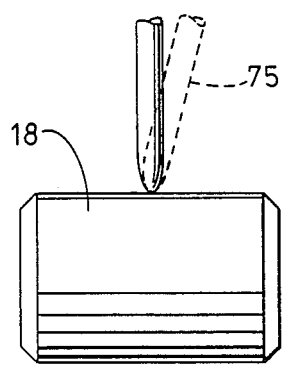
FIG. 4 illustrates the offset from perpendicular to probe positioning which may be necessary in the present invention.

First, the stack 22 of bearings 18A–H is loaded onto the rollers 3A and B. Details of removing roller 3C in order to facilitate this will be later discussed. Next, the eddy current probe 27 is rotated along paths 37 and 48 in FIG. 3 in order to increase the signal produced by the probe 27. When the signal is found to be maximal, or at least satisfactory and non-minimal, sufficient magnetic coupling between the eddy current probe 27 and the bearings 18 is assumed to have been achieved. It may be thought that merely positioning the probe 27 perpendicular to the surface of the bearings 18 will provide maximal magnetic coupling. However, Applicants have found that probe-to-probe variations in the magnetic coils or antennas (not shown) contained within the probes prevents such perpendicular alignment, by itself, from maximizing coupling. Accordingly, Applicants teach that the probe be rotated about pivot points 33 and 36 until signal coupling is maximized. It is pointed out that this can result in positioning of the probe, as shown in exaggerated form in FIG. 4, at the nonperpendicular position shown by phantom probe 75.

The carriage 54 is preferably positioned such that the probe 27 starts at point 78 in FIG. 2. After one revolution of the bearing stack 22, the probe is advanced in the direction of arrow 58B a predetermined distance, a preferably 0.010 inches. Following this advancement, the scanning automatically continues because the bearings 18A–H continue to rotate at the same speed as before. This process of scanning the bearing for a full revolution and then advancing in the direction of arrow 58B for 0.010 inches is continued until all of the bearings in the stack 22 have been scanned.

Figure 5:
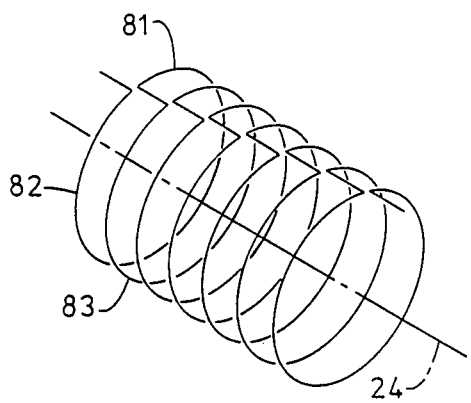
FIGS. 5 and 6 illustrates the path taken by the probe with respect to the bearing surface.

The actual path followed by the probe in scanning the bearings is shown in greater detail in FIG. 5. It is noted that the path segment 81, which is that followed by the probe during the 0.010 inch advancement between the circular scans 82 and 83 is not parallel to the axis 24 because the bearing 18 continues to rotate in the direction of arrow 85 in FIG. 6 while the probe 27 is translating in the 0.010 inch increment 81.

The translation of the carriage 54 along rails 56 and 58 in FIG. 2 is preferably accomplished by a ball screw mechanism 85 such as one available under Model Series R0705-36-FOAAW from Warner Brake & Clutch Co., located in Beloit, Wisc. A Wavetek sweep function generator (not shown) such as Model No. 180, available from Wavetek, located in San Diego, Calif., pulses the stepping motor of the ball screw mechanism 85 at the completion of each full revolution and triggers a drive mechanism (not shown) which drives the ball screw mechanism to advance the carriage 54 to thereby trace the probe along the path segment 81 in FIGS. 5 and 6. A preferred drive mechanism is Model No. M091-FD06, available from Superior Electric, located in Bristol, Conn.

Figure 7:
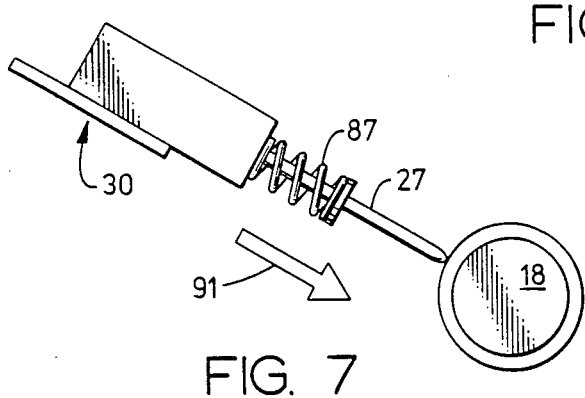
FIG. 7 illustrates spring loading of the probe against a bearing.

As shown in FIG. 7, the probe 27 is spring loaded by spring 87 which urges it in the direction of arrow 91 against the surface of the bearing 18. One purpose of this spring loading is now described with reference to FIG. 8. The bearings 19 have chamfers 94 at their ends. The spring 87 urges the probe 27 in the direction of arrow 91, into contact with the bearing surface, even along chamfers 94, so that the probe 27 generally follows the contour shown by dashed line 99.

Following completion of the scan of the last bearing, that is, when the probe 27 reaches point 101 in FIG. 2, the rotation of the bearing stack 22 is terminated. The bracket 30 is pulled in the direction of arrow 53A by an operator and the rail bed 57 is raised upward in the direction of arrow 68A. The bracket is moved so that the tip 102 of the probe 27 will clear the roller 3C during this upward motion. The rail bed 57 is raised a sufficient distance so that blocks 103 and 104 which support roller 3C can be removed from supports 105 and 107. The blocks 103 and 104 are supported by alignment pins 110 (only one pin is shown at block 103) which mate with holes (not shown) contained in blocks 105 and 107. With the roller 3C removed, bearings 18 can be removed.

Applicants have found that if the bearings 18 are not restrained against moving along the axis 24 (that is, in the direction of arrows 58A and B), then the rotation of the rollers 3A–C will itself cause the bearings 18 to walk along the axis 24. This walking interferes with ascertaining the location of imperfections found by the probe 27, because the exact position of a given bearing 18 is not known at the time of the detection of the flaw. Accordingly, stops 112A and 112B, which are spring loaded, are used to abut neighboring bearings into a stack. The combined result of stops 112A and 112B and resiliently sleeved rollers 3A–C is to cause the stack 22 of bearings to rotate coaxially and in unison.

Applicants have inspected roller bearings of diameter 0.625 inch (dimension 116 in FIG. 1) using rollers 3A–C of mutually identical diameter, namely, dimension 119, which is 0.750 inch, and having a sleeve thickness of 0.125 inch (dimension 121) of the resilient material identified above. The centers of the rollers are spaced such that dimensions 125, 126, and 127 are 1.188, 1.188, and 1.188 inches, respectively.

Figure 9:
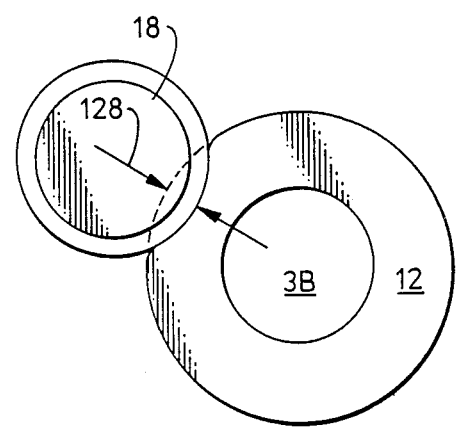
FIG. 9 illustrates the compression of the rollers of the cradle of FIG. 1.

A trigonometric calculation will show that, under the dimensions given above, the resilient sleeves 12 will each be compressed about 0.0016 inches by the bearing 18. This distance is shown as dimension 128 in FIG. 9. This compression serves to promote better frictional contact between the bearing 18 and the sleeve 12.

Figure 6:
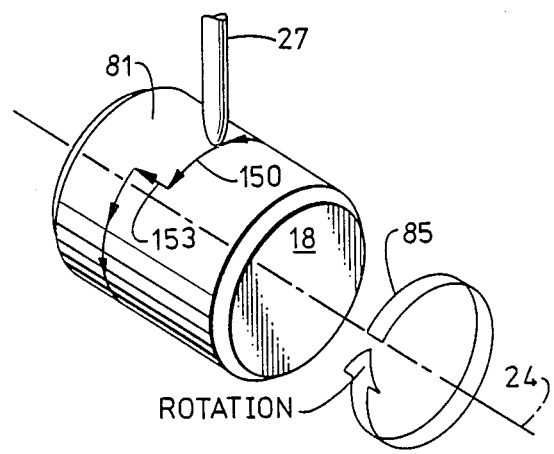
Figure 10:
FIG. 10 is a reproduction of a strip chart recording or probe signals produced by scanning a stack of roller bearings.

Stepwise translation of the probe 27 along increments 81 in FIGS. 5 and 6 has been described. When the probe is translated such that it stands directly above the interface 129 in FIG. 8 between two neighboring bearings, a large flaw signal is detected, as shown in FIG. 10, which is a reproduction of a strip chart recording of the amplitude of the eddy current signal produced by the probe 27 as a function of probe position along the axis 24 in FIG. 2. The interface 129, being viewed as a very thin, very deep crack, produces a very large spike 200 in FIG. 10. Applicants use this fact to flag and identify the bearing currently being scanned. That is, external circuitry, shown as box 135 in FIG. 2, counts the number of large spikes which occur, thereby counting the number of interfaces which the probe 27 has passed, thereby yielding information as to the position in sequence of the bearing currently under scrutiny. For example, having counted 5 spikes indicates that the sixth bearing is currently being examined.

Figure 8:
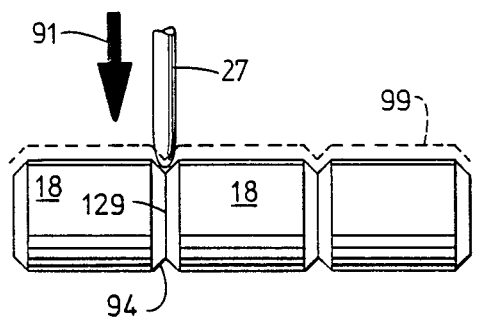
FIG. 8 illustrates the path taken by the probe along the bearing stack.

Stepwise advancement depicted in FIG. 8 has been discussed. It is not necessary that one complete revolution of a bearing be experienced prior to an incremental advancement 81. The advancement of the carriage 54 may be continual and its speed can be a predetermined percentage of the rotational surface speed of the probe 27 along the bearing surface so that a helical pattern (not shown) is traced by the probe 27 along the surface of bearings 18.

Eddy current circuitry and equipment manufactured by Nortec Corporation, located in Kennewick, Wash., has been used. For example, a probe 27 of model number S6E9 has been used. A strip chart recorder of Gould/Brush model number 2000 has been used, together with analyzing circuitry 135 of model number NDT25L has been used.

A strip chart recording has been discussed. This is considered to be a permanent visual record of the signal produced by the eddy current probe, as opposed to a non-permanent record, such as produced by an oscilloscope.

Applicants point out that the directions indicated in FIG. 2 by arrow pairs 53A-B, 58A-B, and 68A-B are mutually perpendicular and that the direction indicated by pair 58A-B is generally parallel to the axis 24.

Applicants further point out that the relative velocity between the bearing surface and the probe 27 in FIG. 6 will increase during the incremental move indicated by path 81. That is, the resultant relative velocity is the sum of the rotational component 150 (which is kept constant) and the axial component 153. Applicants have found that this increase neither deteriorates the signal produced by probe 27, not produces spurious signals which falsely indicate the presence of a flaw.

Numerous modifications and substitutions can be undertaken in applying the principles described without departing from the true spirit and scope of the present invention.

What is desired to be secured by Letters Patent of the United States is the following.

We claim:

1. Apparatus for the examination of cylindrical objects, comprising:
   (a) cradle means for rotating the objects in a coaxial stack;
   (b) means for urging a sensor against the objects; and
   (c) means for advancing the sensor a predetermined increment along the axis after a predetermined amount of rotation of the stack.

2. Apparatus according to claim 1 and further comprising:
   (d) means for maintaining the objects in abutment during rotation and for inhibiting the tendency of the objects to move in the direction of the axis during rotation.

3. Apparatus for the examination of cylindrical objects, comprising:
   (a) cradle means for
      (i) supporting the objects in a coaxial stack and
      (ii) rotating the objects about the axis of the stack;
   (b) carriage means which includes
      (i) a bracket for supporting a probe,
      (ii) biasing means for urging the probe into contact with the objects,
      (iii) a first pivot point about which the probe can rotate in a radial plane of the objects; and
      (iv) a second pivot point about which the probe can rotate in an axial plane of the objects;
   whereby the probe can be positioned at a predetermined angle with respect to the surface of the objects; and
   (c) support means for supporting the carriage such that the carriage can move along a path substantially parallel to the axis of the stack, thereby scanning the probe along the surface of the objects.

4. Apparatus for the examination of roller bearings, comprising:
   (a) cradle means for supporting the bearings, including
      (i) three rollers for surrounding the bearings, each roller comprising a cylinder surrounded by a resilient sleeve, for supporting the bearings in a coaxial stack; and
      (ii) two stops each positionable at one end of the stack for maintaining all bearings in abutment with their neighboring bearings and for preventing motion of the stack along the axis;
   (b) bracket means for supporting an eddy current probe and including
      (i) first pivot means for allowing the probe to rotate in a first plane,
      (ii) second pivot means for allowing the probe to rotate in a second plane, wherein the two pivot means allow the probe to be positioned at a selectable angle with respect to the surface of the bearings, and
      (iii) biasing means for urging the probe against the surface of the bearings;
   (c) first rail means for supporting the bracket and allowing the bracket to travel toward and away from the stack, in a first direction;
   (d) carriage means for supporting the bracket means of (b);
   (e) second rail means carried by a rail bed for supporting the carriage means of (d) and for allowing the carriage means to move the probe in a second direction along the surface of the bearings, along a path generally parallel with the axis of the stack;
   (f) third rail means for supporting the rail bed and for moving the rail bed toward and away from the stack of bearings in a third direction;
   (g) rotation means for rotating at least one of the rollers of (a)(i) for rotating the stack of bearings;
   (h) advancement means for advancing the carriage along the second rail means in a predetermined increment following a predetermined amount of rotation of the bearings;
   (i) strip chart means coupled to the probe of (b) for receiving the probe signal and recording the signal in a record in visual form; and
   (j) sensing means coupled to the probe for sensing the occurrence of a signal produced by the probe at the interface between two adjacent bearings and for associating the portion of the record of (i) with the bearing producing the portion.

5. Apparatus according to claim 4 in which the first, second, and third directions are mutually perpendicular, and the second direction is generally parallel with the axis of the stack.

6. A method of examining the surface of a stack of cylindrical objects, comprising the following steps:
   (a) maintaining the objects in a coaxial stack;
   (b) positioning an eddy current probe against one of the objects;
   (c) observing the output signal of the probe and adjusting the position of the probe with respect to the bearing surface so that the magnitude of the probe signal is non-minimal;
   (d) rotating the stack at a substantially constant speed; and
   (e) after predetermined amounts of rotation of the stack, moving the probe in the direction of the axis a predetermined increment, thereby increasing the relative velocity between the probe and the bearing surface during the incremental move.

7. A method according to claim 6 and further comprising the step of:
   (f) recording the signal produced by the probe in permanent, visual form; and
   (g) identifying a signal produced at an interface of two neighboring bearings and, in response, identifying the portion of the permanent visual form of (f) produced by one of the neighboring bearings.

* * * * *